(12) United States Patent
Flohr et al.

(10) Patent No.: US 7,544,679 B2
(45) Date of Patent: Jun. 9, 2009

(54) 6-OXO-6,7-DIHYDRO-5H-DIBENZO[B,D]-AZEPIN-7-YL DERIVATIVES

(75) Inventors: Alexander Flohr, Reinach BL (CH); Roland Jakob-Roetne, Inzlingen (DE); Wolfgang Wostl, Grenzach-Wyhlen (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/019,667

(22) Filed: Jan. 25, 2008

(65) Prior Publication Data

US 2008/0188463 A1    Aug. 7, 2008

(30) Foreign Application Priority Data

Feb. 2, 2007    (EP)    ................... 07101658

(51) Int. Cl.
C07D 223/18    (2006.01)
A61K 31/55    (2006.01)

(52) U.S. Cl. .................. 514/212.04; 540/522
(58) Field of Classification Search ............ 514/212.04; 540/522
See application file for complete search history.

(56) References Cited

U.S. PATENT DOCUMENTS

| | | | |
|---|---|---|---|
| 6,759,404 B2 | 7/2004 | Olson et al. | |
| 7,160,875 B2 | 1/2007 | Flohr et al. | |

FOREIGN PATENT DOCUMENTS

| | | |
|---|---|---|
| WO | WO 93/03011 | 2/1993 |
| WO | WO 01/27091 | 4/2001 |
| WO | WO 01/77086 | 10/2001 |
| WO | WO 01/90084 | 11/2001 |
| WO | WO 2004/069826 | 8/2004 |
| WO | WO 2005/023772 | 3/2005 |
| WO | WO 2005/040126 | 5/2005 |
| WO | WO 2006/061136 | 6/2006 |
| WO | WO 2007/110335 | 10/2007 |

OTHER PUBLICATIONS

Sisodia et al., Nature Reviews/Neuroscience vol. 3, Apr. 2002, pp. 281-290.
Beher et al., Biochemical Society Transactions (2002), vol. 30, Part 4, pp. 534-537.
Wolfe M., Current Topics in Medicinal Chemistry, 2002, 2, pp. 371-383.
Tsai et al., Current Medicinal Chemistry, 2002, col. 9, No. 11, pp. 1087-1106.
Sambamurti et al., Drug Development Research, vol. 56, 2002, pp. 211-227.
May, P.C., Drug Discovery Today, vol. 6, No. 9, May 2001, pp. 459-462.
Nunan et al., FEBS Letters, 483 (2000) pp. 6-10.
Hardy et al., Science vol. 297, 2002, pp. 353-356.
Wolfe M., Journal of Medicinal Chemistry, vol. 44, No. 13 (2001) pp. 2039-2060.
Brockhaus, et al., Neuroreport 9(7) pp. 1481-1486 (1998).
Li, et al., PNAS vol. 97(11) pp. 6138-6143 (2000).
Dovey et al., Journal of Neurochemistry vol. 76, No. 1 pp. 173-181 (2001).

*Primary Examiner*—Bruck Kifle
(74) *Attorney, Agent, or Firm*—George W. Johnston; Patricia S. Rocha-Tramaloni; Kimberly J. Prior

(57) ABSTRACT

The invention relates to 6-oxo-6,7-dihydro-5H-dibenzo[b,d] azepin-7-yl derivatives of formula I

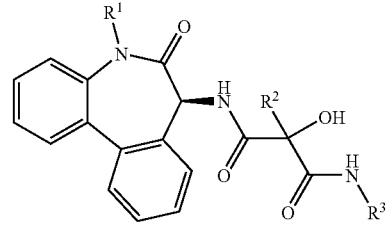

wherein $R^1$, $R^2$ and $R^3$ are as defined herein. The compounds are γ-secretase inhibitors useful in the treatment of Alzheimer's disease or common cancer, including, but not limited to, cervical carcinomas and breast carcinomas and malignancies of the hematopoietic system.

6 Claims, No Drawings

6-OXO-6,7-DIHYDRO-5H-DIBENZO[B,D]-AZEPIN-7-YL DERIVATIVES

PRIORITY TO RELATED APPLICATION(S)

This application claims the benefit of European Patent Application No. 07101658.8, filed Feb. 2, 2007, which is hereby incorporated by reference in its entirety.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length. Abeta peptides are produced from APP through the sequential action of 2 proteolytic enzymes termed β- and β-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. Latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substates and which are themselves polytopic membrane proteins. Other essential components of γ-secretase may be nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch.

The γ-secretase activity is absolutely required for the production of Abeta peptides. This has been shown both by genetic means, i.e., ablation of the presenilin genes and by low-molecular-weight inhibitory compounds. Since according to the amyloid hypothesis of AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:
Nature Reviews/Neuroscience, Vol. 3, April 2002/281,
Biochemical Society Transactions (2002), Vol. 30. part 4,
Current Topics in Medicinal Chemistry, 2002, 2, 371-383,
Current Medicinal Chemistry, 2002, Vol. 9, No. 11, 1087-1106,
Drug Development Research, 56, 211-227, 2002,
Drug Discovery Today, Vol. 6, No. 9, May 2001, 459-462,
FEBS Letters, 483, (2000), 6-10,
Science, Vol. 297, 353-356, July 2002 and
Journal of Medicinal Chemistry, Vol. 44, No. 13, 2001, 2039-2060.

SUMMARY OF THE INVENTION

The invention provides 6-oxo-6,7-dihydro-5H-dibenzo[b,d]azepin-7-yl derivatives of formula I

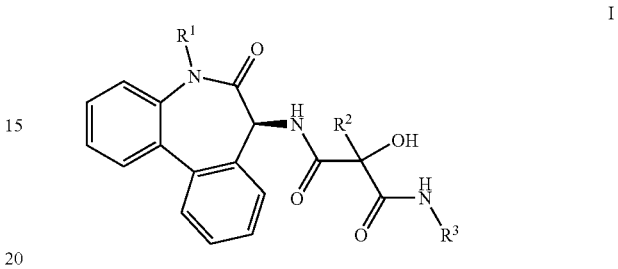

wherein
$R^1$ is hydrogen or lower alkyl substituted by halogen;
$R^2$ is lower alkyl;
$R^3$ is lower alkyl substituted by halogen, —$(CH_2)_n$-cycloalkyl or —$(CH_2)_n$-phenyl, wherein the phenyl ring is unsubstituted or substituted by halogen;
n is 0, 1 or 2;

and to pharmaceutically suitable optically pure epimers or mixtures thereof.

The invention further provides all forms of optically pure epimers or mixtures thereof for compounds of formula I.

The invention provides pharmaceutical compositions which comprise a compound of formula I and a pharmaceutically acceptable carrier. The invention also provides methods for the manufacture of the compounds and compositions of the invention.

The compounds of formula I are γ-secretase inhibitors. Thus, the compounds of this invention will be useful for treating Alzheimer's disease (AD) by blocking the activity of γ-secretase and reducing or preventing the formation of the various amyloidogenic Abeta peptides. Compounds of the invention also may be useful in the treatment of common cancers, including, but not limited to, cervical carcinomas and breast carcinomas and malignancies of the hematopoietic system. The advantage of compounds of formula I for use in a drug is their improved γ-secretase inhibition, together with their good thermodynamic solubility in comparison with compounds, disclosed in WO 2005/023772.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain alkyl group containing from 1 to 7 carbon atoms, for example, methyl, ethyl, propyl, isopropyl, n-butyl, i-butyl, 2-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example $CF_3$, $CHF_2$, $CH_2F$, CH₂CF₃, CH₂CH₂F, CH₂CF₂CF₃, CH₂CF₂CH₃, CH₂CH₂CF₂CF₃, CH₂CH₂CF₃, CH₂CH₂CH₂CF₃ and those lower alkyl substituted by halogen groups which are illustrated by the compounds of the examples hereinafter.

The term "cycloalkyl" denotes a not aromatic carbon ring, containing 3 to 6 carbon atoms, for example cyclopropyl, cyclopentyl or cyclohexyl. A preferred cycloalkyl is cyclopropyl.

"Pharmaceutically acceptable," such as pharmaceutically acceptable carrier, excipient, etc., means pharmacologically acceptable and substantially non-toxic to the subject to which the particular compound is administered.

"Therapeutically effective amount" means an amount that is effective to prevent, alleviate or ameliorate symptoms of disease or prolong the survival of the subject being treated.

The invention provides 6-oxo-6,7-dihydro-5H-dibenzo[b,d]azepin-7-yl derivatives of formula I

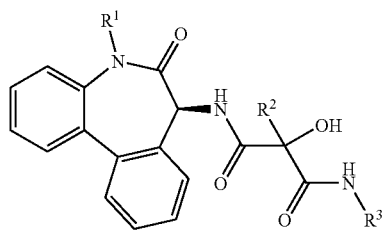

I wherein
R¹ is hydrogen or lower alkyl substituted by halogen;
R² is lower alkyl;
R³ is lower alkyl substituted by halogen, —(CH₂)ₙ-cycloalkyl or —(CH₂)ₙ-phenyl, wherein the phenyl ring is unsubstituted or substituted by halogen;
n is 0, 1 or 2;

and to pharmaceutically suitable optically pure epimers or mixtures thereof.

The invention further provides all forms of optically pure epimers or mixtures thereof for compounds of formula I.

Preferred compounds of formula I are those, wherein R¹ is hydrogen and R³ is lower alkyl substituted by halogen, for example the following compounds:
(R/S)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide,
(R)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide,
(S)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide,
(R/S)-2-hydroxy-2-methyl-N-((S)-6-oxo-6,7-dihydro-5H-dibenzo[b,d]azepin-7-yl)-N'-(3,3,3-trifluoro-propyl)-malonamide,
(S)-2-hydroxy-2-methyl-N-((S)-6-oxo-6,7-dihydro-5H-dibenzo[b,d]azepin-7-yl)-N'-(3,3,3-trifluoro-propyl)-malonamide,
(R)-2-ethyl-2-hydroxy-N-((S)-6-oxo-6,7-dihydro-5H-dibenzo[b,d]azepin-7-yl)-N'-(2,2,2-trifluoro-ethyl)-malonamide,
(R/S)-2-hydroxy-N-((S)-6-oxo-6,7-dihydro-5H-dibenzo[b,d]azepin-7-yl)-N-(2,2,3,3,3-pentafluoro-propyl)-2-propyl-malonamide,
(R)-2-hydroxy-N-((S)-6-oxo-6,7-dihydro-5H-dibenzo[b,d]azepin-7-yl)-N-(2,2,3,3,3-pentafluoro-propyl)-2-propyl-malonamide or
(S)-2-hydroxy-N-((S)-6-oxo-6,7-dihydro-5H-dibenzo[b,d]azepin-7-yl)-N-(2,2,3,3,3-pentafluoro-propyl)-2-propyl-malonamide.

Preferred compounds of formula I are further those, wherein R¹ is lower alkyl substituted by halogen and R³ is lower alkyl substituted by halogen, for example the following compounds:
(R)-2-hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide or
(S)-2-hydroxy-2-methyl-N-[(S)-6-oxo-5-(2,2,2-trifluoro-ethyl)-6,7-dihydro-5H-dibenzo[b,d]azepin-7-yl]-N'-(2,2,2-trifluoro-ethyl)-malonamide.

The present compounds of formula I and their pharmaceutically acceptable salts can be prepared by methods known in the art, for example, by processes described below, which processes comprise a) reacting a compound of formula

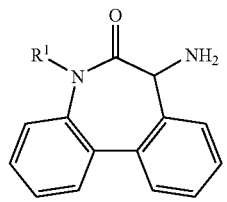

II with a compound of formula

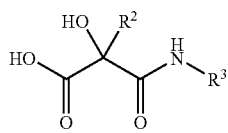

III to obtain a compound of formula

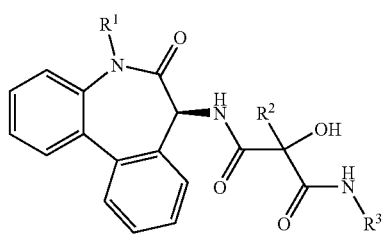

I wherein the substituents have the meaning as described above or, b) reacting a compound of formula

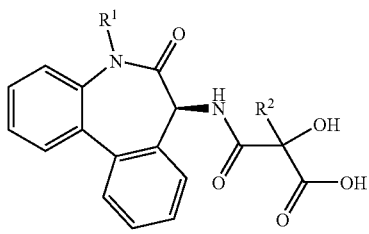

IV with an amine of formula

NH₂R³ to obtain a compound of formula

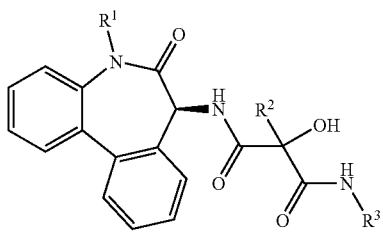

I wherein the substituents have the meaning as described above, and, if desired, converting a mixture of epimeric forms of a compound of formula I (R/S) into epimer (R) and epimer (S).

The detailed description can be found below and in Examples 1-14. The starting material of a compound of formula II is a known compound and the amine of formula III can be prepared as described in scheme 2.

Scheme 1

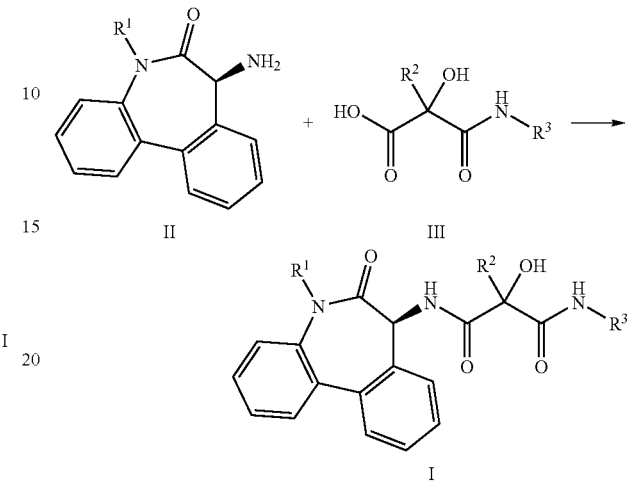

A solution of a compound of formula II and a compound of formula III in a solvent, such as tetrahydrofuran is reacted at room temperature with 1-hydroxy-benzotriazole hydrate, diisopropylethylamine and N-(3-dimethylaminopropyl)-N'-ethyl-carbodiimide hydrochloride. Stirring is continued overnight. Removal of the solvent by distillation and chromatography on silicagel with ethylacetate/heptane yields a compound of formula I.

Scheme 2

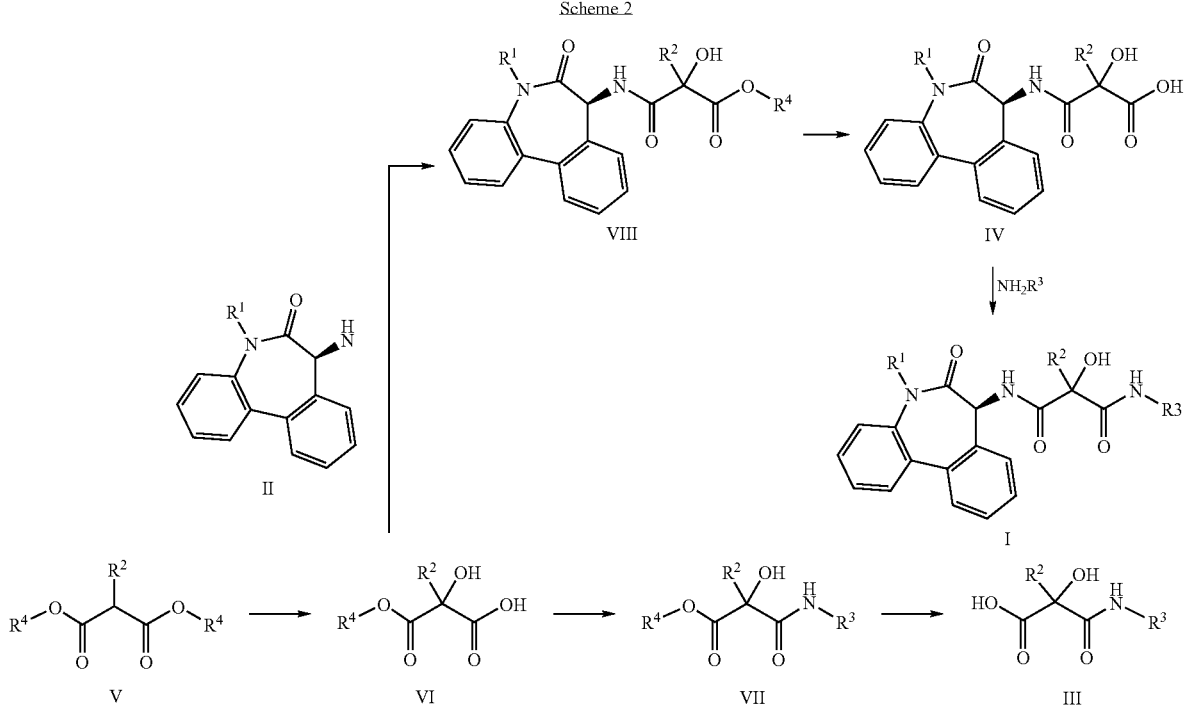

R⁴ = lower alkyl

Preparation of a Compound of Formula III

Air is bubbled through a suspension of dialkylpropylmalonate of formula V and cesium carbonate in dimethylformamide. At about 10-20° C. water is added and stirring is continued at room temperature for about 3 hours. The dimethylformamide is then removed. Water is added and the extraction with diethylether yielded the monoalkylester of formula VI.

The monoalkylester of formula VI is dissolved in tetrahydrofurane and cooled to 0° C. 1-Hydroxy-benzotriazole hydrate, diisopropylethylamine and N-(3-dimethylaminopropyl)-N'-ethyl-carbodiimide hydrochloride are added and stirring is continued for about 4 days at room temperature. Then aqueous hydrochloric acid is added. After extraction and purification a compound of formula VII is obtained.

The obtained mixture of epimeric forms of a compound of formula VII can be separated into the epimers R and S by chromatography on Chiralpak AD with isopropanol/heptane 10/90 in usual manner.

The acid of formula III can be prepared as follows: A solution of lithium hydroxide in water is stirred with a compound of formula VII in tetrahydrofuran, first eluting enantiomer of the previous step, over night at room temperature. Extraction first with water/diethylether and then with aqueous hydrochloric acid/ethylacetate yielded the desired acid of formula III.

Preparation of a Compound of Formula I

A solution of 7-amino-5H,7H-dibenzo[b,d]azepin-6-one of formula II and a compound of formula VI in tetrahydrofuran is cooled to 0° C., and 1-hydroxy-benzotriazole hydrate, diisopropylethylamine and N-(3-dimethylaminopropyl)-N'-ethyl-carbodiimide hydrochloride are added. Stirring is continued overnight at room temperature. After removal of the solvent by distillation and chromatography a compound of formula VIII is obtained.

A mixture of the obtained compound of formula VIII in tetrahydrofuran and of lithiumhydroxide in water is then stirred overnight at room temperature. The solvent is evaporated and the residue is extracted to the acid of formula V.

Then a solution of a compound of formula V and a corresponding amine in tetrahydrofuran is cooled to 0° C. and 1-hydroxy-benzotriazole hydrate, diisopropylethylamine and N-(3-dimethylaminopropyl)-N'-ethyl-carbodiimide hydrochloride are added. Stirring is continued overnight. Removal of the solvent by distillation and chromatography on silicagel leads to the desired compound of formula I.

The present compounds have two stereo centers. They may exist in a mixture of epimeric forms. One is always the S-epimer, the other may be R, S or RS epimers. Separation into the desired epimeric form can be effected according to methods known per se either at an early stage of the synthesis or, preferably, at a later stage by separation of the diastereomeric products by chromatography.

The compounds were investigated in accordance with the test given hereinafter.

Description of γ-secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6×Histidin tail for purification which is expressed in *E.coli* in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138-6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481-1486 (1998).

The preferred compounds show a $IC_{50}$<700 (nM). In the list below are described the data to the γ-secretase inhibition:

| Example No. | $IC_{50}$ in vitro (nM) |
|---|---|
| 1a (R/S) | 4 |
| 1b (R) | 2 |
| 1c (S) | 3 |
| 2a (R/S) | 10 |
| 2b (R) | 38 |
| 2c (S) | 5 |
| 3a (R) | 260 |
| 3b (S) | 11 |
| 4a (R/S) | 89 |
| 4b (S) | 8 |
| 5c (R/S) | 110 |
| 6a (R/S) | 15 |
| 6g (R or S) | 118 |
| 6h (S or R) | 50 |
| 7a (R/S) | 6 |
| 7b (R) | 4 |
| 7c (S) | 5 |
| 8d (R/S) | 15 |
| 9 (R/S) | 630 |
| 10 (R/S) | 41 |
| 11a (R/S) | 136 |
| 11b (R) | 13 |
| 12a (R/S) | 11 |
| 12b (R) | 3.5 |
| 13a (R) | 480 |
| 13b (S) | 5 |
| 14 (R/S) | 30 |

In addition, the compounds of the present invention have been tested in a THESA assay for determination of the thermodynamic solubility.

THESA Assay:

Approximately 2 mg of each compound was added in excess to a 50 mM phosphate buffer, at room temperature (22.5±1° C.). Each sample was placed in a microanalysis tube, which was sonicated for 1 h and agitated for 2 h. All suspensions were left overnight. At the next day all pHs were measured with a pH-meter and the samples filtered with a micronic filterplate (MSGVN2250) to separate the solid material from the solution. Then, all solutions were analyzed by HPLC. The calibration line was established by different concentrations of the compound in DMSO. From this regression equation the solubility of the compound was determined.

From the table below it can be seen that the compounds of the present invention have a better solubility or activity when compared with WO2005/023772.

| Example No. present appl. | $IC_{50}$/THESA (µg/ml) | Corresponding Example from WO 2005/023772 | $IC_{50}$/THESA (µg/ml) | Comments |
|---|---|---|---|---|
| 1b | 5/19 | | 2/<1 | Similar potency, higher solubility |
| 1c | 3/14 | | 6/<1 | Similar potency, higher solubility |
| 2c | 5/127 | | 120/<1 | Higher potency, higher solubility |
| 3b | 11/26 | | 150/16 | Higher potency, higher solubility |
| 6a | 15/— | | 610/— | Higher potency |
| 6g | 118/— | | nearly inactive/— | Higher potency |

-continued

| Example No. present appl. | IC$_{50}$/THESA (µg/ml) | Corresponding Example from WO 2005/023772 | IC$_{50}$/THESA (µg/ml) | Comments |
|---|---|---|---|---|
| 12a | 11/— | [structure: F$_3$C-N-benzazepinone-NH-CO-CH$_2$-CO-NH-CH$_2$-C(CF$_3$)(F)$_2$] | 480/— | Higher potency |
| 13b | 5/14 | [structure: F$_3$C-N-benzazepinone-NH-CO-CH$_2$-CO-NH-CH$_2$-CF$_3$] | 38/— | Higher potency |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

In accordance with the invention compounds of formula I are useful in the control or prevention of illnesses based on the inhibition of the γ-secretase, such as of Alzheimer's disease or cancer.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |

-continued

Capsule Formulation

| Item | Ingredients | mg/capsule | | | |
|---|---|---|---|---|---|
| | | 5 mg | 25 mg | 100 mg | 500 mg |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLE 1

(R/S)-2-Hydroxy-2-methyl-N-((S)-6-oxo-6,7-dihydro-5H-dibenzo[b,d]azepin-7-yl)-N'-(2,2,3,3,3-pentafluoro-propyl)-malonamide and (R)-2-Hydroxy-2-methyl-N-((S)-6-oxo-6,7-dihydro-5H-dibenzo[b,d]azepin-7-yl)-N'-(2,2,3,3,3-pentafluoro-propyl)-malonamide and (S)-2-Hydroxy-2-methyl-N-((S)-6-oxo-6,7-dihydro-5H-dibenzo[b,d]azepin-7-yl)-N'-(2,2,3,3,3-pentafluoro-propyl)-malonamide

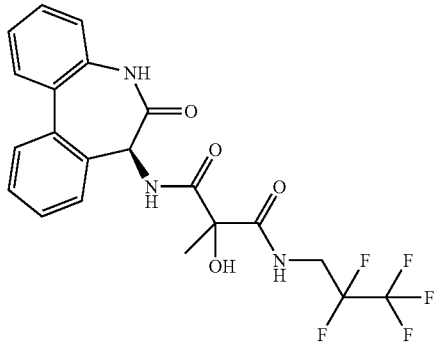

a) (R/S)-2-Hydroxy-2-methyl-N-((S)-6-oxo-6,7-dihydro-5H-dibenzo[b,d]azepin-7-yl)-N'-(2,2,3,3,3-pentafluoro-propyl)-malonamide A solution of 101 mg (0.45 mmol) (S)-7-amino-5H,7H-dibenzo[b,d]azepin-6-one and 119 mg (0.45 mmol) (RS)-2-hydroxy-2-methyl-N-(2,2,3,3,3-pentafluoro-propyl)-malonamic acid in 15 ml tetrahydrofuran were cooled to 0° C. and 61.8 mg (0.45 mmol) 1-hydroxy-benzotriazole hydrate, 157 μl (0.90 mmol) diisopropylethylamine and 87.6 mg (0.45 mmol) N-(3-dimethylaminopropyl)-N'-ethyl-carbodiimide hydrochloride were added. Stirring was continued overnight at room temperature. The mixture was poured on ice/water and 1 N aqueous hydrochloric acid was added until pH=1 was reached. Extraction with diethylether, washing with saturated aqueous sodium hydrogen carbonate solution and brine and chromatography on silicagel with ethylacetate/cyclohexane 1/1 yielded 86.1 mg (41%) (R/S)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide as a white solid, MS (m/e): 472.1 (M+H)$^+$.

b) (R)-2-Hydroxy-2-methyl-N-((S)-6-oxo-6,7-dihydro-5H-dibenzo[b,d]azepin-7-yl)-N'-(2,2,3,3,3-pentafluoro-propyl)-malonamide and c) (S)-2-Hydroxy-2-methyl-N-((S)-6-oxo-6,7-dihydro-5H-dibenzo[b,d]azepin-7-yl)-N'-(2,2,3,3,3-pentafluoro-propyl)-malonamide A mixture of 124 mg (0.27 mmol) of the epimeric (R/S)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide was separated by preparative HPLC on YMC Pack SIL with heptane/ethanol/isopropanol/acetonitril mixture to yield 11 mg (R or S)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide, epimer A (first eluting), MS (m/e): 469.9 (M−H)$^-$, and 19 mg (S or R)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide, epimer B (second eluting), MS (m/e): 472.1 (M+H)$^+$.

EXAMPLE 2

(R/S)-2-Hydroxy-2-methyl-N-((S)-6-oxo-6,7-dihydro-5H-dibenzo[b,d]azepin-7-yl)-N'-(3,3,3-trifluoro-propyl)-malonamide and (R)-2-Hydroxy-2-methyl-N-((S)-6-oxo-6,7-dihydro-5H-dibenzo[b,d]azepin-7-yl)-N'-(3,3,3-trifluoro-propyl)-malonamide and (S)-2-Hydroxy-2-methyl-N-((S)-6-oxo-6,7-dihydro-5H-dibenzo[b,d]azepin-7-yl)-N'-(3,3,3-trifluoro-propyl)-malonamide

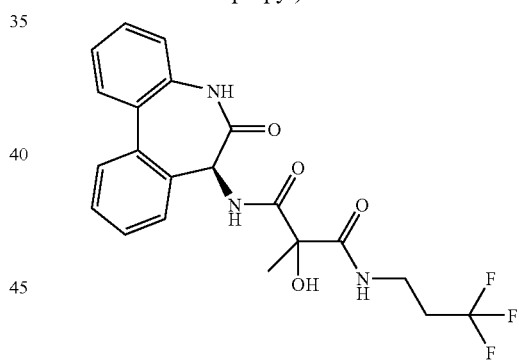

a) (R/S)-2-hydroxy-2-methyl-N-((S)-6-oxo-6,7-dihydro-5H-dibenzo[b,d]azepin-7-yl)-N'-(3,3,3-trifluoro-propyl)-malonamide A solution of 210 mg (0.94 mmol) (S)-7-amino-5H,7H-dibenzo[b,d]azepin-6-one and 215 mg (0.94 mmol) (RS)-2-hydroxy-2-methyl-N-(3,3,3-trifluoro-propyl)-malonamic acid in 50 ml tetrahydrofuran were cooled to 0° C. and 129 mg (0.94 mmol) 1-hydroxy-benzotriazole hydrate, 327 μl (1.87 mmol) diisopropylethylamine and 183 mg (0.94 mmol) N-(3-dimethylaminopropyl)-N'-ethyl-carbodiimide hydrochloride were added. Stirring was continued overnight at room temperature. The mixture was poured on ice/water and 1 N aqueous hydrochloric acid was added until pH=1 was reached. Extraction with first diethylether and second with ethylacetate, washing with saturated aqueous sodium hydrogen carbonate solution and brine and chromatography on silicagel with ethylacetate/heptane 2/1 yielded 150 mg (41%) (R/S)-

2-hydroxy-2-methyl-N-((S)-6-oxo-6,7-dihydro-5H-dibenzo[b,d]azepin-7-yl)-N'-(3,3,3-trifluoro-propyl)-malonamide as a white solid, MS (m/e): 436.1 (M+H)+.

b) (R)-2-Hydroxy-2-methyl-N-((S)-6-oxo-6,7-dihydro-5H-dibenzo[b,d]azepin-7-yl)-N'-(3,3,3-trifluoro-propyl)-malonamide and c) (S)-2-Hydroxy-2-methyl-N-((S)-6-oxo-6,7-dihydro-5H-dibenzo[b,d]azepin-7-yl)-N'-(3,3,3-trifluoro-propyl)-malonamide A mixture of 150 mg (mmol) of the epimeric (R/S)-2-hydroxy-2-methyl-N-((S)-6-oxo-6,7-dihydro-5H-dibenzo[b,d]azepin-7-yl)-N'-(3,3,3-trifluoro-propyl)-malonamide was separated by preparative HPLC on Chiralpak AD with ethanol/heptane 20/80 to yield 60 mg (R or S)-2-hydroxy-2-methyl-N-((S)-6-oxo-6,7-dihydro-5H-dibenzo[b,d]azepin-7-yl)-N'-(3,3,3-trifluoro-propyl)-malonamide, epimer A (first eluting), MS (m/e): 436.1 (M+H)+, and 75 mg (S or R)-2-hydroxy-2-methyl-N-((S)-6-oxo-6,7-dihydro-5H-dibenzo[b,d]azepin-7-yl)-N'-(3,3,3-trifluoro-propyl)-malonamide, epimer B (second eluting), MS (m/e): 436.1 (M+H)+.

EXAMPLE 3

(R)-2-Hydroxy-2-methyl-N-((S)-6-oxo-6,7-dihydro-5H-dibenzo[b,d]azepin-7-yl)-N'-(2,2,2-trifluoro-ethyl)-malonamide and (S)-2-Hydroxy-2-methyl-N-((S)-6-oxo-6,7-dihydro-5H-dibenzo[b,d]azepin-7-yl)-N'-(2,2,2-trifluoro-ethyl)-malonamide

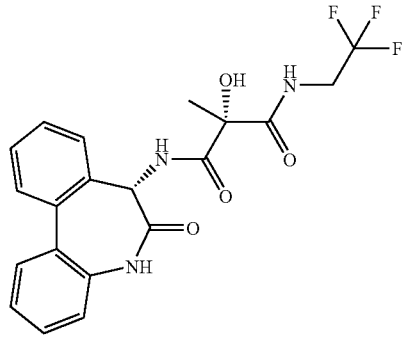

a) (R)-2-Hydroxy-2-methyl-N-((S)-6-oxo-6,7-dihydro-5H-dibenzo[b,d]azepin-7-yl)-N'-(2,2,2-trifluoro-ethyl)-malonamide A solution of 70.0 mg (0.31 mmol) (S)-7-amino-5H,7H-dibenzo[b,d]azepin-6-one and 73.9 mg (0.34 mmol) (R)-2-hydroxy-2-methyl-N-(2,2,2-trifluoro-ethyl)-malonamic acid in 6 ml tetrahydrofuran were cooled to 0° C. and 46.4 mg (0.34 mmol) 1-hydroxy-benzotriazole hydrate, 117 µl (0.69 mmol) diisopropylethylamine and 65.8 mg (0.34 mmol) N-(3-dimethylaminopropyl)-N'-ethyl-carbodiimide hydrochloride were added. Stirring was continued for 16 hours. Removal of the solvent by distillation and chromatography on silicagel with heptane/ethylacetate (gradient 100/0 to 25/75) yielded 101 mg (77%) (R)-2-hydroxy-2-methyl-N-((S)-6-oxo-6,7-dihydro-5H-dibenzo[b,d]azepin-7-yl)-N'-(2,2,2-trifluoro-ethyl)-malonamide, MS (m/e): 422.0 (M+H)+.

b) (S)-2-Hydroxy-2-methyl-N-((S)-6-oxo-6,7-dihydro-5H-dibenzo[b,d]azepin-7-yl)-N'-(2,2,2-trifluoro-ethyl)-malonamide

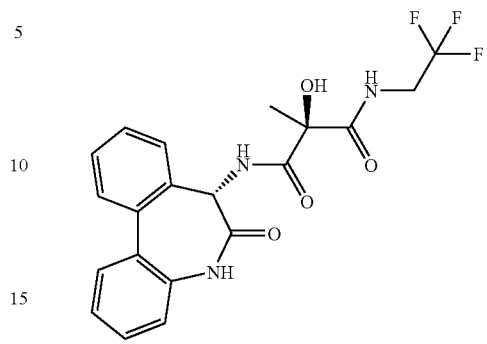

A solution of 70.0 mg (0.31 mmol) (S)-7-amino-5H,7H-dibenzo[b,d]azepin-6-one and 73.9 mg (0.34 mmol) (S)-2-hydroxy-2-methyl-N-(2,2,2-trifluoro-ethyl)-malonamic acid in 6 ml tetrahydrofuran were cooled to 0° C. and 46.4 mg (0.34 mmol) 1-hydroxy-benzotriazole hydrate, 117 µl (0.69 mmol) diisopropylethylamine and 65.8 mg (0.34 mmol) N-(3-dimethylaminopropyl)-N'-ethyl-carbodiimide hydrochloride were added. Stirring was continued for 16 hours. Removal of the solvent by distillation and chromatography on silicagel with heptane/ethylacetate (gradient 100/0 to 25/75) yielded 104 mg (79%) (S)-2-hydroxy-2-methyl-N-((S)-6-oxo-6,7-dihydro-5H-dibenzo[b,d]azepin-7-yl)-N'-(2,2,2-trifluoro-ethyl)-malonamide, MS (m/e): 422.0 (M+H)+.

EXAMPLE 4

(R/S)-2-Ethyl-2-hydroxy-N-((S)-6-oxo-6,7-dihydro-5H-dibenzo[b,d]azepin-7-yl)-N'-(2,2,2-trifluoro-ethyl)-malonamide and (R)-2-Ethyl-2-hydroxy-N-((S)-6-oxo-6,7-dihydro-5H-dibenzo[b,d]azepin-7-yl)-N'-(2,2,2-trifluoro-ethyl)-malonamide and (S)-2-Ethyl-2-hydroxy-N-((S)-6-oxo-6,7-dihydro-5H-dibenzo[b,d]azepin-7-yl)-N'-(2,2,2-trifluoro-ethyl)-malonamide Chiral

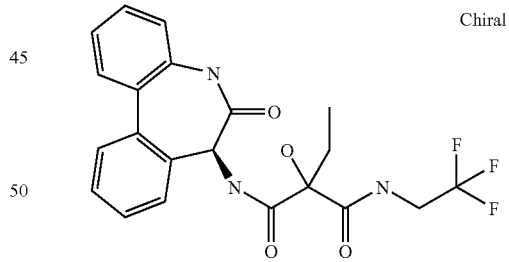

a) (R/S)-2-Ethyl-2-hydroxy-N-((S)-6-oxo-6,7-dihydro-5H-dibenzo[b,d]azepin-7-yl)-N'-(2,2,2-trifluoro-ethyl)-malonamide A solution of 250 mg (1.12 mmol) (S)-7-amino-5H,7H-dibenzo[b,d]azepin-6-one and 256 mg (1.12 mmol) (RS)-2-hydroxy-2-(2,2,2-trifluoro-ethylcarbamoyl)-butyric acid in 24 ml tetrahydrofuran were cooled to 0° C. and 174 mg (0.94 mmol) 1-hydroxy-benzotriazole hydrate, 390 µl (2.23 mmol) diisopropylethylamine and 218 mg (1.12 mmol) N-(3-dimethylaminopropyl)-N'-ethyl-carbodiimide hydrochloride were added. Stirring was continued overnight at room temperature. Removal of the solvent by distillation and chromatography on silicagel with ethylacetate/heptane 2/8 yielded 330 mg (68%) (R/S)-2-ethyl-2-hydroxy-N-((S)-6-oxo-6,7-dihydro-5H-dibenzo[b,d]azepin-7-yl)-N'-(2,2,2-trifluoro-ethyl)-malonamide as a colorless oil, MS (m/e): 436.1 (M+H)$^+$.

b) (R)-2-Ethyl-2-hydroxy-N-((S)-6-oxo-6,7-dihydro-5H-dibenzo[b,d]azepin-7-yl)-N'-(2,2,2-trifluoro-ethyl)-malonamide and c) (S)-2-Ethyl-2-hydroxy-N-((S)-6-oxo-6,7-dihydro-5H-dibenzo[b,d]azepin-7-yl)-N'-(2,2,2-trifluoro-ethyl)-malonamide A mixture of 310 mg (mmol) of the epimeric (R/S)-2-ethyl-2-hydroxy-N-((S)-6-oxo-6,7-dihydro-5H-dibenzo[b,d]azepin-7-yl)-N'-(2,2,2-trifluoro-ethyl)-malonamide was separated by preparative HPLC on Chiralpak AD with isopropanol/heptane 15/85 to yield 120 mg (R or S)-2-ethyl-2-hydroxy-N-((S)-6-oxo-6,7-dihydro-5H-dibenzo[b,d]azepin-7-yl)-N'-(2,2,2-trifluoro-ethyl)-malonamide, epimer A (first eluting), MS (m/e): 436.1 (M+H)$^+$, and 120 mg (S or R)-2-ethyl-2-hydroxy-N-((S)-6-oxo-6,7-dihydro-5H-dibenzo[b,d]azepin-7-yl)-N'-(2,2,2-trifluoro-ethyl)-malonamide, epimer B (second eluting), MS (m/e): 436.1 (M+H)$^+$.

EXAMPLE 5

(R/S)-N-Cyclopropylmethyl-2-hydroxy-N-((S)-6-oxo-6,7-dihydro-5H-dibenzo[b,d]azepin-7-yl)-2-propyl-malonamide

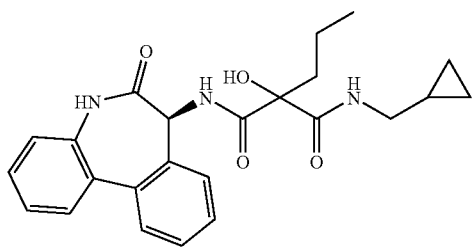

a) (R/S)-2-Hydroxy-2-((S)-6-oxo-6,7-dihydro-5H-dibenzo[b,d]azepin-7-ylcarbamoyl)-pentanoic acid ethyl ester

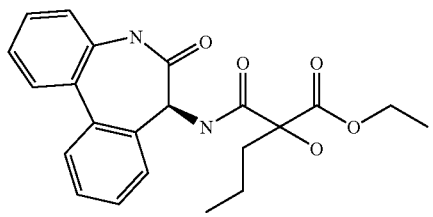

A solution of 500 mg (2 mmol) (S)-7-amino-5H,7H-dibenzo[b,d]azepin-6-one and 466 mg (2 mmol) (RS)-2-hydroxy-2-propyl-malonic acid monoethyl ester in 40 ml tetrahydrofuran were cooled to 0° C. and 331 mg (2 mmol) 1-hydroxy-benzotriazole hydrate, 830 μl (5 mmol) diisopropylethylamine and 470 mg (2 mmol) N-(3-dimethylaminopropyl)-N'-ethyl-carbodiimide hydrochloride were added. Stirring was continued overnight at room temperature. Removal of the solvent by distillation and chromatography on silicagel with heptane/ethylacetate (gradient 90/10 to 50/50) yielded 630 mg (71%) (R/S)-2-hydroxy-2-((S)-6-oxo-6,7-dihydro-5H-dibenzo[b,d]azepin-7-ylcarbamoyl)-pentanoic acid ethyl ester as a colorless foam, MS (m/e): 397.3 (M+H)$^+$.

b) (R/S)-2-Hydroxy-2-((S)-6-oxo-6,7-dihydro-5H-dibenzo[b,d]azepin-7-ylcarbamoyl)-pentanoic acid

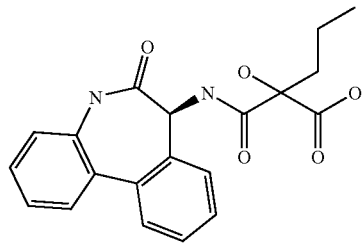

A mixture of 600 mg (2 mmol) (R/S)-2-hydroxy-2-((S)-6-oxo-6,7-dihydro-5H-dibenzo[b,d]azepin-7-ylcarbamoyl)-pentanoic acid ethyl ester in 8 ml tetrahydrofuran and of 70.0 mg (2 mmol) lithiumhydroxide in 4 ml water was stirred overnight at room temperature. The solvent was evaporated and the residue extracted at pH 1 with ethylacetate to yield 450 mg (81%) (R/S)-2-hydroxy-2-((S)-6-oxo-6,7-dihydro-5H-dibenzo[b,d]azepin-7-ylcarbamoyl)-pentanoic acid, MS (m/e): 367.1 (M−H)$^-$.

c) (R/S)-N-Cyclopropylmethyl-2-hydroxy-N-((S)-6-oxo-6,7-dihydro-5H-dibenzo[b,d]azepin-7-yl)-2-propyl-malonamide A solution of 70.0 mg (0.19 mmol) 2-hydroxy-2-((S)-6-oxo-6,7-dihydro-5H-dibenzo[b,d]azepin-7-ylcarbamoyl)-pentanoic acid and 14.9 mg (0.21 mmol) cyclopropanmethylamine in 3 ml tetrahydrofuran were cooled to 0° C. and 28.2 mg (0.21 mmol) 1-hydroxy-benzotriazole hydrate, 71 μl (0.42 mmol) diisopropylethylamine and 40.1 mg (0.21 mmol) N-(3-dimethylaminopropyl)-N'-ethyl-carbodiimide hydrochloride were added. Stirring was continued overnight. Removal of the solvent by distillation and chromatography on silicagel with heptane/ethylacetate (gradient 90:10 to 50:50) yielded 50.0 mg (62%) (R/S)-N-cyclopropylmethyl-2-hydroxy-N-((S)-6-oxo-6,7-dihydro-5H-dibenzo[b,d]azepin-7-yl)-2-propyl-malonamide: MS (m/e): 422.4 (M+H)$^+$.

EXAMPLE 6

(R/S)-2-Hydroxy-N-((S)-6-oxo-6,7-dihydro-5H-dibenzo[b,d]azepin-7-yl)-2-propyl-N-(3,3,3-trifluoro-propyl)-malonamide and (R)-2-Hydroxy-N-((S)-6-oxo-6,7-dihydro-5H-dibenzo[b,d]azepin-7-yl)-2-propyl-N-(3,3,3-trifluoro-propyl)-malonamide and

(S)-2-Hydroxy-N-((S)-6-oxo-6,7-dihydro-5H-dibenzo[b,d]azepin-7-yl)-2-propyl-N-(3,3,3-trifluoro-propyl)-malonamide

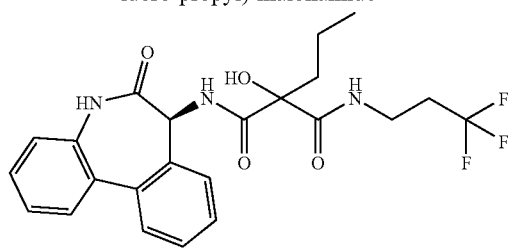

a) (R/S)-2-Hydroxy-N-((S)-6-oxo-6,7-dihydro-5H-dibenzo[b,d]azepin-7-yl)-2-propyl-N-(3,3,3-trifluoro-propyl)-malonamide A solution of 70.0 mg (0.19 mmol) 2-hydroxy-2-((S)-6-oxo-6,7-dihydro-5H-dibenzo[b,d]azepin-7-ylcarbamoyl)- pentanoic acid and 31.3 mg (0.21 mmol) 3,3,3-trifluoropropylamine hydrochloride in 3 ml tetrahydrofuran were cooled to 0° C. and 28.2 mg (0.21 mmol) 1-hydroxy-benzotriazole hydrate, 103 μl (0.61 mmol) diisopropylethylamine and 40.1 mg (0.21 mmol) N-(3-dimethylaminopropyl)-N'-ethyl-carbodiimide hydrochloride were added. Stirring was continued overnight. Removal of the solvent by distillation and chromatography on silicagel with heptane/ethylacetate (gradient 90:10 to 50:50) yielded 50.0 mg (57%) (R/S)-2-hydroxy-N-((S)-6-oxo-6,7-dihydro-5H-dibenzo[b,d]azepin-7-yl)-2-propyl-N-(3,3,3-trifluoro-propyl)-malonamide: MS (m/e): 464.0 (M+H)$^+$.

b) 2-Hydroxy-2-propyl-malonic acid monoethyl ester

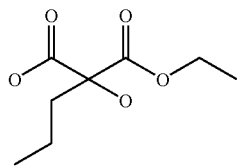

Air was bubbled for 1 hour at room temperature through a suspension of 15.0 g (72.7 mmol) diethylpropylmalonate and 47.6 g (145 mmol) cesium carbonate in 120 ml dimethylformamide. At 10-20° C. 150 ml water were added and stirring was continued at room temperature for 3 hours. Most of the dimethylformamide was then removed by vacuum distillation at 35° C. bath temperature. 1 l water was added and extraction with diethylether yielded 11.7 g 2-hydroxy-2-propyl-malonic acid monoethylester, MS (m/e): 189.1 (M–H)$^-$.

c) 2-Hydroxy-2-(3,3,3-trifluoropropylcarbamoyl) pentanoic acid ethylester

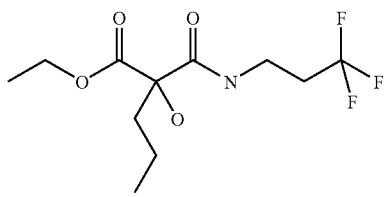

An amount of 4.03 g (~21 mmol) of the 2-hydroxy-2-propyl-malonic acid monoethylester was dissolved in 200 ml tetrahydrofurane and cooled to 0° C. 2.92 g (21.2 mmol) 1-hydroxy-benzotriazole hydrate, 12.9 ml (74.1 mmol) diisopropylethylamine and 4.14 g (21.2 mmol) N-(3-dimethylaminopropyl)-N'-ethyl-carbodiimide hydrochloride were added and stirring was continued for 4 days at room temperature. 45 ml 2 N aqueous hydrochloric acid were added. Extraction with ethylacetate, washing with brine and chromatography on silicagel with ethylacetate/cyclohexane 3/1 yielded 4.60 g (76%) 2-hydroxy-2-(3,3,3-trifluoropropylcarbamoyl)pentanoic acid ethylester as yellow oil, MS (m/e): 286.1 (M+H)$^+$.

d) (R and S)-2-Hydroxy-2-(3,3,3-trifluoropropylcarbamoyl)pentanoic acid ethylester The racemic 2-hydroxy-2-(3,3,3-trifluoropropylcarbamoyl)pentanoic acid ethylester was separated into the enantiomers by chromatography on Chiralpak AD with isopropanol/heptane 10/90 to yield 0.96 g (21%) of (R or S)-2-hydroxy-2-(3,3,3trifluoropropylcarbamoyl)pentanoic acid ethylester, as first eluting enantiomer, MS (m/e): 286.1 (M+H)$^+$, and 1.09 g (24%) of (S or R)-2-hydroxy-2-(3,3,3-trifluoropropylcarbamoyl)pentanoic acid ethylester, as second eluting enantiomer, MS (m/e): 286.4 (M+H)$^+$.

e) (R or S )-2-Hydroxy-2-(3,3,3-trifluoro-propylcarbamoyl)-pentanoic acid, entity A

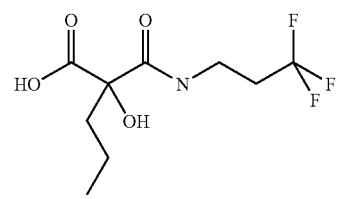

A solution of 131 mg (3.09 mmol) lithium hydroxide in 8 ml water was stirred with 880 mg (3.09 mmol) (R or S)-2-hydroxy-2-(3,3,3trifluoropropylcarbamoyl)pentanoic acid ethylester in 18 ml tetrahydrofuran, first eluting enantiomer of the previous step, over night at room temperature. Extraction first with water/diethylether and then with 1 N aqueous hydrochloric acid/ethylacetate yielded 744 mg (93%) (R or S)-2-hydroxy-2-(3,3,3-trifluoro-propylcarbamoyl)-pentanoic acid, entity A, MS (m/e): 256.1 (M–H)$^-$.

f) (S or R)-2-Hydroxy-2-(3,3,3-trifluoro-propylcarbamoyl)-pentanoic acid, entity B A solution of 158 mg (3.72 mmol) lithium hydroxide in 8.5 ml water was stirred with 1.06 g (3.72 mmol) (S or R)-2-hydroxy-2-(3,3,3trifluoropropylcarbamoyl)pentanoic acid ethylester, second eluting enantiomer of step c), over night at room temperature. Extraction first with water/diethylether and then with 1 N aqueous hydrochloric acid/ethylacetate yielded 870 mg (91%) (S or R )-2-hydroxy-2-(3,3,3-trifluoropropylcarbamoyl)-pentanoic acid, entity B, MS (m/e): 256.1 (M–H)$^-$.

g) (R or S)-2-Hydroxy-N-((S)-6-oxo-6,7-dihydro-5H-dibenzo[b,d]azepin-7-yl)-2-propyl-N-(3,3,3-trifluoro-propyl)-malonamide, entity A A solution of 135 mg (0.60 mmol) (S)-7-amino-5H,7H-dibenzo[b,d]azepin-6-one, and 154 mg (0.60 mmol) (R or S )-2-hydroxy-2-(3,3,3-trifluoro-propylcarbamoyl)-pentanoic acid, entity A, in 10 ml tetrahydrofuran were cooled to 0° C. and 93.8 mg (0.60 mmol) 1-hydroxy-benzotriazole hydrate, 210 μl (1.20 mmol) diisopropylethylamine and 117 mg (0.60 mmol) N-(3-dimethylaminopropyl)-N'-ethyl-carbodiimide hydrochloride were added. Stirring was continued overnight. Removal of the solvent by distillation and chromatography on silicagel with ethylacetate/heptane (gradient 10:90 to 100:0) yielded 218 mg (78%) (R or S)-2-hydroxy-N-((S)-6-oxo-6, 7-dihydro-5H-dibenzo[b,d]azepin-7-yl)-2-propyl-N-(3,3,3-trifluoro-propyl)-malonamide, entity A: MS (m/e): 462.0 (M–H)$^-$.

h) (S or R)-2-Hydroxy-N-((S)-6-oxo-6,7-dihydro-5H-dibenzo[b,d]azepin-7-yl)-2-propyl-N-(3,3,3-trifluoro-propyl)-malonamide, entity B A solution of 135 mg (0.60 mmol) (S)-7-amino-5H,7H-dibenzo[b,d]azepin-6-one, and 154 mg (0.60 mmol) (S or R)-2-hydroxy-2-(3,3,3-trifluoro-propylcarbamoyl)-pentanoic acid, entity B, in 10 ml tetrahydrofuran were cooled to 0° C. and 93.8 mg (0.60 mmol) 1-hydroxy-benzotriazole hydrate, 210 μl (1.20 mmol) diisopropylethylamine and 117 mg (0.60 mmol) N-(3-dimethylaminopropyl)-N'-ethyl-carbodiimide hydrochloride were added. Stirring was continued overnight. Removal of the solvent by distillation and chromatography on silicagel with ethylacetate/heptane (gradient 10:90 to 100:0) yielded 221 mg (80%) (S or R)-2-hydroxy-N-((S)-6-oxo-6,7-dihydro-5H-dibenzo[b,d]azepin-7-yl)-2-propyl-N-(3,3,3-trifluoro-propyl)-malonamide, entity B: MS (m/e): 462.0 (M–H)⁻.

EXAMPLE 7

(R/S)-2-Hydroxy-N-((S)-6-oxo-6,7-dihydro-5H-dibenzo[b,d]azepin-7-yl)-N-(2,2,3,3,3-pentafluoro-propyl)-2-propyl-malonamide and (R)-2-Hydroxy-N-((S)-6-oxo-6,7-dihydro-5H-dibenzo[b,d]azepin-7-yl)-N-(2,2,3,3,3-pentafluoro-propyl)-2-propyl-malonamide and (S)-2-Hydroxy-N-((S)-6-oxo-6,7-dihydro-5H-dibenzo[b,d]azepin-7-yl)-N-(2,2,3,3,3-pentafluoro-propyl)-2-propyl-malonamide

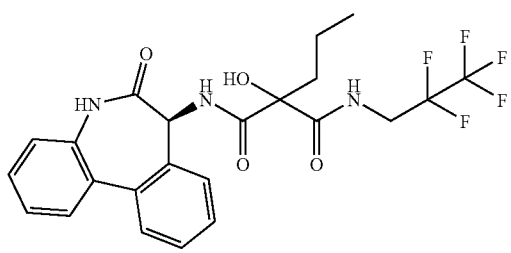

a) (R/S)-2-Hydroxy-N-((S)-6-oxo-6,7-dihydro-5H-dibenzo[b,d]azepin-7-yl)-N-(2,2,3,3,3-pentafluoro-propyl)-2-propyl-malonamide A solution of 70.0 mg (0.19 mmol) 2-hydroxy-2-((S)-6-oxo-6,7-dihydro-5H-dibenzo[b,d]azepin-7-ylcarbamoyl)-pentanoic acid and 31.2 mg (0.21 mmol) 2,2,3,3,3-pentafluoropropylamine in 3 ml tetrahydrofuran were cooled to 0° C. and 28.2 mg (0.21 mmol) 1-hydroxy-benzotriazole hydrate, 72 μl (0.42 mmol) diisopropylethylamine and 40.1 mg (0.21 mmol) N-(3-dimethylaminopropyl)-N'-ethyl-carbodiimide hydrochloride were added. Stirring was continued overnight. Removal of the solvent by distillation and chromatography on silicagel with heptane/ethylacetate (gradient 90:10 to 50:50) yielded 60.0 mg (63%) (R/S)-2-hydroxy-N-((S)-6-oxo-6,7-dihydro-5H-dibenzo[b,d]azepin-7-yl)-N-(2,2,3,3,3-pentafluoro-propyl)-2-propyl-malonamide: MS (m/e): 500.4 (M+H)⁺.

b) (R)-2-Hydroxy-N-((S)-6-oxo-6,7-dihydro-5H-dibenzo[b,d]azepin-7-yl)-N-(2,2,3,3,3-pentafluoro-propyl)-2-propyl-malonamide and c) (S)-2-Hydroxy-N-((S)-6-oxo-6,7-dihydro-5H-dibenzo[b,d]azepin-7-yl)-N-(2,2,3,3,3-pentafluoro-propyl)-2-propyl-malonamide A mixture of 500 mg (1.0 mmol) of the epimeric (R/S)-2-hydroxy-N-((S)-6-oxo-6,7-dihydro-5H-dibenzo[b,d]azepin-7-yl)-N-(2,2,3,3,3-pentafluoro-propyl)-2-propyl-malonamide was separated by preparative HPLC on Chiralpak AD with heptane/ethanol 90:10 to yield 115 mg (22%) (R or S)-2-hydroxy-N-((S)-6-oxo-6,7-dihydro-5H-dibenzo[b,d]azepin-7-yl)-N-(2,2,3,3,3-pentafluoro-propyl)-2-propyl-malonamide, epimer A (first eluting), MS (m/e): 500.4 (M+H)⁺, and 95 mg (19%) (S or R)-2-hydroxy-N-((S)-6-oxo-6,7-dihydro-5H-dibenzo[b,d]azepin-7-yl)-N-(2,2,3,3,3-pentafluoro-propyl)-2-propyl-malonamide, epimer B (second eluting), MS (m/e): 500.4 (M+H)⁺.

EXAMPLE 8

(R/S)-2-Hydroxy-2-isobutyl-N-((S)-6-oxo-6,7-dihydro-5H-dibenzo[b,d]azepin-7-yl)-N-(2,2,3,3,3-pentafluoro-propyl)-malonamide

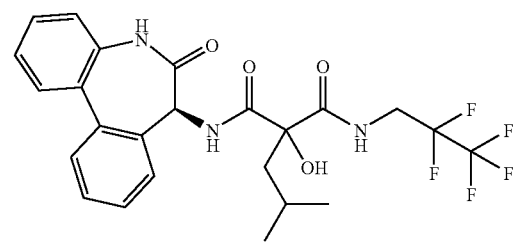

a) (R/S)-2-Hydroxy-2-isobutyl-malonic acid monomethyl ester

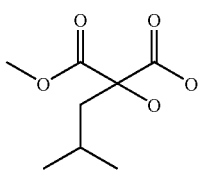

Air was bubbled for 1 hour at room temperature through a suspension of 0.5 g (3 mmol) dimethyl-(2-methylpropyl)malonate and 1.73 g (5 mmol) cesium carbonate in 7 ml dimethylformamide. Stirring was continued at room temperature for 24 hours. 25 ml water was added and the mixture was extracted with diethylether. Acidification with aqueous 1 N hydrochloric acid to pH=1 and extraction with ethylacetate yielded 0.42 g (83%) (R/S)-2-hydroxy-2-isobutyl-malonic acid monomethyl ester, MS (m/e): 189.4 (M–H)⁻.

b) (R/S)-2-Hydroxy-4-methyl-2-((S)-6-oxo-6,7-dihydro-5H-dibenzo[b,d]azepin-7-ylcarbamoyl)-pentanoic acid methyl ester

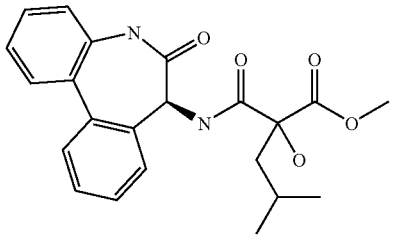

A solution of 350 mg (1.56 mmol) (S)-7-amino-5H,7H-dibenzo[b,d]azepin-6-one and 327 mg (1.72 mmol) (R/S)-2-hydroxy-2-isobutyl-malonic acid monomethyl ester in 30 ml tetrahydrofuran were cooled to 0° C. and 232 mg (1.72 mmol) 1-hydroxy-benzotriazole hydrate, 584 μl (3.43 mmol) diisopropylethylamine and 329 mg (192 mmol) N-(3-dimethylaminopropyl)-N'-ethyl-carbodiimide hydrochloride were added. Stirring was continued overnight at room temperature. Extraction with water/ethylacetate and chromatography on silicagel with heptane/ethylacetate (gradient 90/10 to 50/50) yielded 470 mg (76%) (R/S)-2-hydroxy-4-methyl-2-((S)-6-oxo-6,7-dihydro-5H-dibenzo[b,d]azepin-7-ylcarbamoyl)-pentanoic acid methyl ester as a colorless foam, MS (m/e): 397.3 (M+H)⁺.

c) (R/S)-2-Hydroxy-4-methyl-2-((S)-6-oxo-6,7-dihydro-5H-dibenzo[b,d]azepin-7-ylcarbamoyl)-pentanoic acid

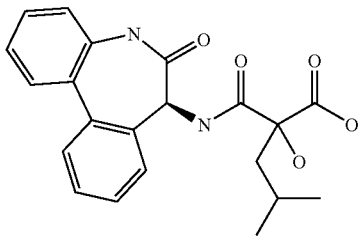

A mixture of 430 mg (1.09 mmol) (R/S)-2-hydroxy-4-methyl-2-((S)-6-oxo-6,7-dihydro-5H-dibenzo[b,d]azepin-7-ylcarbamoyl)-pentanoic acid methyl ester in 6 ml tetrahydrofuran and of 50.1 mg (1.19 mmol) lithiumhydroxide monohydrate in 3 ml water was stirred overnight at room temperature. The solvent was evaporated and the residue extracted at pH 1 with ethylacetate to yield 390 mg (94%) (R/S)-2-hydroxy-4-methyl-2-((S)-6-oxo-6,7-dihydro-5H-dibenzo[b,d]azepin-7-ylcarbamoyl)-pentanoic acid, MS (m/e): 381.0 (M–H)⁻.

d) (R/S)-2-Hydroxy-2-isobutyl-N-((S)-6-oxo-6,7-dihydro-5H-dibenzo[b,d]azepin-7-yl)-N-(2,2,3,3,3-pentafluoro-propyl)-malonamide A solution of 50.0 mg (0.13 mmol) 2-hydroxy-4-methyl-2-((S)-6-oxo-6,7-dihydro-5H-dibenzo[b,d]azepin-7-ylcarbamoyl)-pentanoic acid and 39.0 mg (0.26 mmol) 2,2,3,3,3-pentafluoropropylamine in 1.5 ml dimethylformamid was cooled to 0° C. and 20 μl (0.14 mmol) triethylamine and 54.5 mg (0.14 mmol) O-(benzotriazol-1-yl)-N,N,N',N'-tetramethyluronium hexafluorophosphate (HBTU) were added. Stirring was continued overnight. Removal of the solvent by distillation and chromatography on silicagel with heptane/ethylacetate (gradient 19:1 to 1:1) yielded 45.0 mg (67%) (R/S)-2-hydroxy-2-isobutyl-N-((S)-6-oxo-6,7-dihydro-5H-dibenzo[b,d]azepin-7-yl)-N-(2,2,3,3,3-pentafluoro-propyl)-malonamide: MS (m/e): 514.5 (M+H)⁺.

EXAMPLE 9

(R/S)-N-Cyclopropylmethyl-2-hydroxy-2-isobutyl-N-((S)-6-oxo-6,7-dihydro-5H-dibenzo[b,d]azepin-7-yl)-malonamide

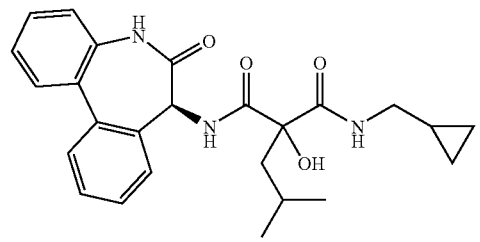

A solution of 50.0 mg (0.13 mmol) 2-hydroxy-4-methyl-2-((S)-6-oxo-6,7-dihydro-5H-dibenzo[b,d]azepin-7-ylcarbamoyl)-pentanoic acid and 18.6 mg (0.26 mmol) cyclopropanmethylamine in 1.5 ml dimethylformamid were cooled to 0° C. and 20 μl (0.14 mmol) triethylamine and 54.5 mg (0.14 mmol) O-(benzotriazol-1-yl)-N,N,N',N'-tetramethyluronium hexafluorophosphate (HBTU) were added. Stirring was continued over the weekend at room temperature. Removal of the solvent by distillation and chromatography on silicagel with heptane/ethylacetate (gradient 19:1 to 1:1) yielded 10.0 mg (18%) (R/S)-N-cyclopropylmethyl-2-hydroxy-2-isobutyl-N-((S)-6-oxo-6,7-dihydro-5H-dibenzo[b,d]azepin-7-yl)-malonamide MS (m/e): 436.1 (M+H)⁺.

EXAMPLE 10

(R/S)-N-(3,5-Difluoro-benzyl)-2-hydroxy-2-isobutyl-N-((S)-6-oxo-6,7-dihydro-5H-dibenzo[b,d]azepin-7-yl)-malonamide

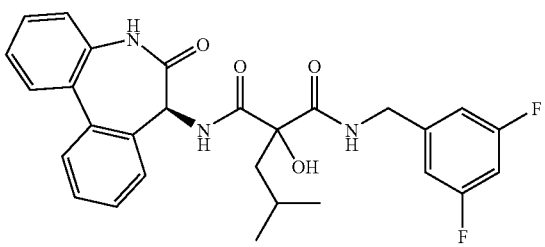

A solution of 50.0 mg (0.13 mmol) 2-hydroxy-4-methyl-2-((S)-6-oxo-6,7-dihydro-5H-dibenzo[b,d]azepin-7-ylcarbamoyl)-pentanoic acid and 37.4 mg (0.26 mmol) 3,5-difluorobenzylamine in 1.5 ml dimethylformamid were cooled to 0° C. and 20 μl (0.14 mmol) triethylamine and 54.5 mg (0.14 mmol) O-(benzotriazol-1-yl)-N,N,N',N'-tetramethyluronium hexafluorophosphate (HBTU) were added. Stirring was continued overnight at room temperature. Removal of the solvent by distillation and chromatography on silicagel with heptane/ethylacetate (gradient 19:1 to 1:1) yielded 10.0 mg (15%) (R/S)-N-(3,5-difluoro-benzyl)-2-hydroxy-2-isobutyl-N-((S)-6-oxo-6,7-dihydro-5H-dibenzo[b,d]azepin-7-yl)-malonamide, MS (m/e): 508.5 (M+H)+.

EXAMPLE 11

(R/S)-2-Hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide, and (R)-2-Hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide and (S)-2-Hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide

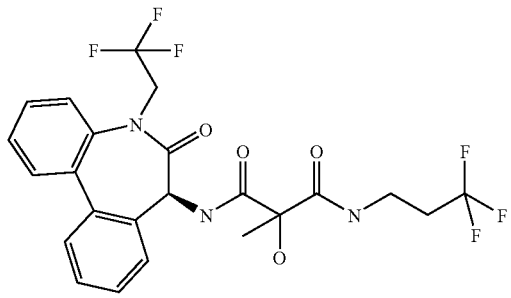

a) (R/S)-2-Hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide A solution of 200 mg (0.65 mmol) (S)-7-amino-5-(2,2,2-trifluoro-ethyl)-5H,7H-dibenzo[b,d]azepin-6-one and 150 mg (0.65 mmol) (RS)-2-hydroxy-2-methyl-N-(3,3,3-trifluoro-propyl)-malonamic acid in 7 ml tetrahydrofuran were cooled to 0° C. and 102 mg (0.65 mmol) 1-hydroxy-benzotriazole hydrate, 228 μl (1.31 mmol) diisopropylethylamine and 128 mg (0.65 mmol) N-(3-dimethylaminopropyl)-N'-ethyl-carbodiimide hydrochloride were added. Stirring was continued overnight at room temperature. Removal of the solvent by distillation and chromatography on silicagel with ethylacetate/heptane (gradient 1/4 to 4/1) yielded 220 mg (65%) (R/S)-2-hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide as a white solid, MS (m/e): 518.2 (M+H)+.

b) (R)-2-Hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide, and c) (S)-2-Hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide, A mixture of 200 mg of the epimeric (R/S)-2-hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide was separated by preparative HPLC on Chiralpak AD with isopropanol/heptane 15/85 to yield 90 mg (R or S)-2-hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide, epimer A (first eluting), MS (m/e): 518.5 (M+H)+, and 90 mg (S or R)-2-hydroxy-2-methyl-N-[(S)-6-oxo-5-(2,2,2-trifluoro-ethyl)-6,7-dihydro-5H-dibenzo[b,d]azepin-7-yl]-N'-(3,3,3-trifluoro-propyl)-malonamide, epimer B (second eluting), MS (m/e): 518.5 (M+H)+.

EXAMPLE 12

(R/S)-2-Hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide, and (R)-2-Hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide and (S)-2-Hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide

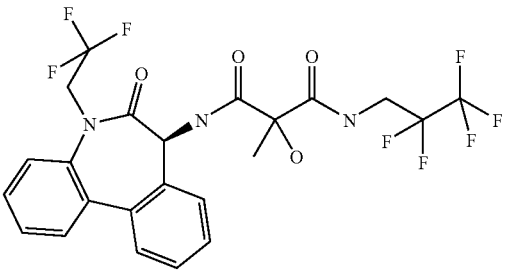

a) (R/S)-2-Hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide A solution of 144 mg (0.47 mmol) (S)-7-amino-5-(2,2,2-trifluoro-ethyl)-5H,7H-dibenzo[b,d]azepin-6-one and 125 mg (0.47 mmol) (RS)-2-hydroxy-2-methyl-N-(2,2,3,3,3-pentafluoro-propyl)-malonamic acid in 21 ml tetrahydrofuran were reacted at room temperature with 73.6 mg (0.47 mmol) 1-hydroxy-benzotriazole hydrate, 165 μl (0.94 mmol) diisopropylethylamine and 92.1 mg (0.47 mmol) N-(3-dimethylaminopropyl)-N'-ethyl-carbodiimide hydrochloride. Stirring was continued overnight. Removal of the solvent by distillation and chromatography on silicagel with ethylacetate/heptane (gradient 15/85 to 40/60) yielded 207 mg (79%) (R/S)-2-hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide as a white solid, MS (m/e): 554.3 (M+H)+.

b) (R)-2-Hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide and c) (S)-2-Hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide The mixture of the epimeric (R/S)-2-hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide was separated by preparative HPLC on Chiralcel OD with isopropanol/heptane 10/90 to yield 40 mg (R or S)-2-hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide, epimer A (first eluting), MS (m/e): 554.3 (M+H)$^+$, and 40 mg (S or R)-2-hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide, epimer B (second eluting), MS (m/e): 554.3 (M+H)$^+$.

EXAMPLE 13

(R)-2-Hydroxy-2-methyl-N-[(S)-6-oxo-5-(2,2,2-trifluoro-ethyl)-6,7-dihydro-5H-dibenzo[b,d]azepin-7-yl]-N'-(2,2,2-trifluoro-ethyl)-malonamide and (S)-2-Hydroxy-2-methyl-N-[(S)-6-oxo-5-(2,2,2-trifluoro-ethyl)-6,7-dihydro-5H-dibenzo[b,d]azepin-7-yl]-N'-(2,2,2-trifluoro-ethyl)-malonamide

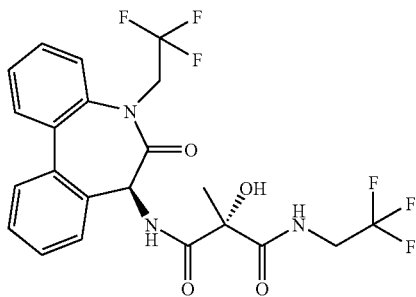

a) (R)-2-Hydroxy-2-methyl-N-[(S)-6-oxo-5-(2,2,2-trifluoro-ethyl)-6,7-dihydro-5H-dibenzo[b,d]azepin-7-yl]-N'-(2,2,2-trifluoro-ethyl)-malonamide and A solution of 75.0 mg (0.25 mmol) (S)-7-amino-5H,7H-dibenzo[b,d]azepin-6-one and 52.7 mg (0.25 mmol) (R)-2-hydroxy-2-methyl-N-(2,2,2-trifluoro-ethyl)-malonamic acid in 7 ml tetrahydrofuran were cooled to 0° C. and 33.8 mg (0.25 mmol) 1-hydroxy-benzotriazole hydrate, 86 µl (0.49 mmol) diisopropylethylamine and 47.9 mg (0.25 mmol) N-(3-dimethylaminopropyl)-N'-ethyl-carbodiimide hydrochloride were added. Stirring was continued for 16 hours. Removal of the solvent by distillation and chromatography on silicagel with heptane/ethylacetate (gradient 10/90 to 40/60) yielded 37 mg (30%) (R)-2-hydroxy-2-methyl-N-[(S)-6-oxo-5-(2,2,2-trifluoro-ethyl)-6,7-dihydro-5H-dibenzo[b,d] azepin-7-yl]-N'-(2,2,2-trifluoro-ethyl)-malonamide, MS (m/e): 504.4 (M+H)$^+$.

b) (S)-2-Hydroxy-2-methyl-N-[(S)-6-oxo-5-(2,2,2-trifluoro-ethyl)-6,7-dihydro-5H-dibenzo[b,d]azepin-7-yl]-N'-(2,2,2-trifluoro-ethyl)-malonamide

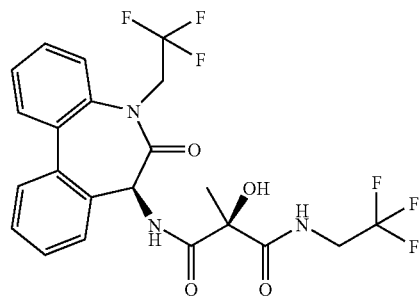

A solution of 75.0 mg (0.25 mmol) (S)-7-amino-5H,7H-dibenzo[b,d]azepin-6-one and 52.7 mg (0.25 mmol) (S)-2-hydroxy-2-methyl-N-(2,2,2-trifluoro-ethyl)-malonamic acid in 7 ml tetrahydrofuran were cooled to 0° C. and 33.8 mg (0.25 mmol) 1-hydroxy-benzotriazole hydrate, 86 µl (0.49 mmol) diisopropylethylamine and 47.9 mg (0.25 mmol) N-(3-dimethylaminopropyl)-N'-ethyl-carbodiimide hydrochloride were added. Stirring was continued overnight. Removal of the solvent by distillation and chromatography on silicagel with heptane/ethylacetate (gradient 10/90 to 40/60) yielded 38 mg (31%) (S)-2-hydroxy-2-methyl-N-[(S)-6-oxo-5-(2,2,2-trifluoro-ethyl)-6,7-dihydro-5H-dibenzo[b,d] azepin-7-yl]-N'-(2,2,2-trifluoro-ethyl)-malonamide, MS (m/e): 504.4 (M+H)$^+$.

EXAMPLE 14

(R/S)-N-(2,2-Difluoro-propyl)-2-hydroxy-N-((S)-6-oxo-6,7-dihydro-5H-dibenzo[b,d]azepin-7-yl)-2-propyl-malonamide

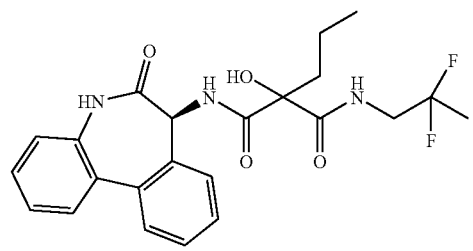

A solution of 50.0 mg (0.14 mmol) 2-hydroxy-2-((S)-6-oxo-6,7-dihydro-5H-dibenzo[b,d]azepin-7-ylcarbamoyl)-pentanoic acid and 14.2 mg (0.15 mmol) 2,2-difluoropropylamine in 2.5 ml tetrahydrofuran were cooled to 0° C. and 20.2 mg (0.15 mmol) 1-hydroxy-benzotriazole hydrate, 39 µl (0.3 mmol) diisopropylethylamine and 28.6 mg (0.15 mmol) N-(3-dimethylaminopropyl)-N'-ethyl-carbodiimide hydrochloride were added. Stirring was continued overnight. Removal of the solvent by distillation and chromatography on silicagel with heptane/ethylacetate (gradient 90:10 to 50:50) yielded 30.0 mg (50%) (R/S)-N-(2,2-Difluoro-propyl)-2-hydroxy-N-((S)-6-oxo-6,7-dihydro-5H-dibenzo[b,d]azepin-7-yl)-2-propyl-malonamide: MS (m/e): 446.1 (M+H)$^+$.

The invention claimed is:
1. A compound of formula I

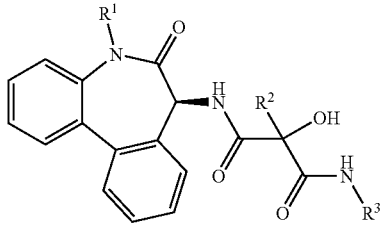

wherein
$R^1$ is hydrogen or lower alkyl substituted by halogen;
$R^2$ is lower alkyl;
$R^3$ is lower alkyl substituted by halogen, —$(CH_2)_n$-cycloalkyl or —$(CH_2)_n$-phenyl, wherein the phenyl ring is unsubstituted or substituted by halogen;
n is 0, 1 or 2;
or a pharmaceutically suitable optically pure epimer or mixture thereof.

2. The compound of claim 1, wherein $R^1$ is hydrogen and $R^3$ is lower alkyl substituted by halogen.

3. The compound of claim 2, selected from the group consisting of
(R/S)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide,
(R)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide,
(S)-2-hydroxy-2-methyl-N-((S)-6-oxo-6,7-dihydro-5H-dibenzo[b,d]azepin-7-yl)-N'-(2,2,3,3,3-pentafluoro-propyl)-malonamide,
(R/S)-2-hydroxy-2-methyl-N-((S)-6-oxo-6,7-dihydro-5H-dibenzo[b,d]azepin-7-yl)-N'-(3,3,3-trifluoro-propyl)-malonamide,
(S)-2-hydroxy-2-methyl-N-((S)-6-oxo-6,7-dihydro-5H-dibenzo[b,d]azepin-7-yl)-N'-(3,3,3-trifluoro-propyl)-malonamide,
(R)-2-ethyl-2-hydroxy-N-((S)-6-oxo-6,7-dihydro-5H-dibenzo[b,d]azepin-7-yl)-N'-(2,2,2-trifluoro-ethyl)-malonamide,
(R/S)-2-hydroxy-N-((S)-6-oxo-6,7-dihydro-5H-dibenzo[b,d]azepin-7-yl)-N-(2,2,3,3,3-pentafluoro-propyl)-2-propyl-malonamide,
(R)-2-hydroxy-N-((S)-6-oxo-6,7-dihydro-5H-dibenzo[b,d]azepin-7-yl)-N-(2,2,3,3,3-pentafluoro-propyl)-2-propyl-malonamide and
(S)-2-hydroxy-N-((S)-6-oxo-6,7-dihydro-5H-dibenzo[b,d]azepin-7-yl)-N-(2,2,3,3,3-pentafluoro-propyl)-2-propyl-malonamide.

4. The compound of claim 1, wherein $R^1$ is lower alkyl substituted by halogen and $R^3$ is lower alkyl substituted by halogen.

5. The compound of claim 4, selected from the group consisting of
(R)-2-hydroxy-2-methyl-N-[(S)-6-oxo-5-(2,2,2-trifluoro-ethyl)-6,7-dihydro-5H-dibenzo[b,d]azepin-7-yl]-N-(2,2,3,3,3-pentafluoro-propyl)-malonamide and
(S)-2-hydroxy-2-methyl-N-[(S)-6-oxo-5-(2,2,2-trifluoro-ethyl)-6,7-dihydro-5H-dibenzo[b,d]azepin-7-yl]-N'-(2,2,2-trifluoro-ethyl)-malonamide.

6. A pharmaceutical composition comprising a therapeutically effective amount of a compound of formula I

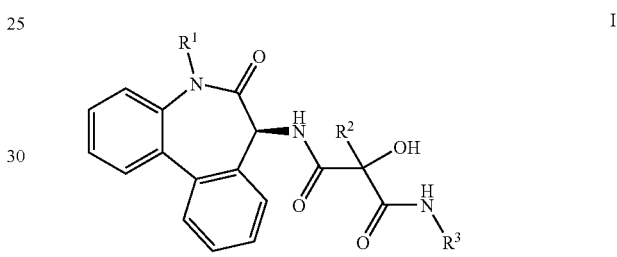

wherein
$R^1$ is hydrogen or lower alkyl substituted by halogen;
$R^2$ is lower alkyl;
$R^3$ is lower alkyl substituted by halogen, —$(CH_2)_n$-cycloalkyl or —$(CH_2)_n$-phenyl, wherein the phenyl ring is unsubstituted or substituted by halogen;
n is 0, 1 or 2;
or a pharmaceutically suitable optically pure epimer or mixture thereof and a pharmaceutically acceptable carrier.

* * * * *